(12) United States Patent
Peyman

(10) Patent No.: US 6,733,750 B1
(45) Date of Patent: May 11, 2004

(54) PROCESS AND COMPOSITION FOR INDUCING POSTERIOR VITREOUS DETACHMENT

(75) Inventor: Gholam A. Peyman, New Orleans, LA (US)

(73) Assignee: Minu, L.L.C., Pittsboro, NC (US)

( * ) Notice: Subject to any disclaimer, the term of this patent is extended or adjusted under 35 U.S.C. 154(b) by 0 days.

(21) Appl. No.: 09/265,532

(22) Filed: Mar. 9, 1999

(51) Int. Cl.[7] .............................................. A61K 38/49
(52) U.S. Cl. ............................... 424/94.63; 424/94.64; 424/94.2; 604/51; 128/898
(58) Field of Search .......................... 128/898; 604/51; 424/94.63, 94.64, 94.2

(56) References Cited

U.S. PATENT DOCUMENTS

| | | | |
|---|---|---|---|
| 5,292,509 A | 3/1994 | Hageman | 424/94.61 |
| 5,304,118 A | 4/1994 | Trese et al. | 605/51 |
| 5,722,428 A | 3/1998 | Kaplan et al. | 128/898 |
| 5,767,079 A | 6/1998 | Glaser et al. | 514/12 |

OTHER PUBLICATIONS

Arthur C. Guyton, Textbook of Medical Physiology, 6th Ed., WB Saunders Co., Phila., pp. 98–99, 1981.*

Chemical Abstracts 124(13):164726w, 1996.*

Alex Jalkh, MD et al., "Prognostic Value of Vitreous Findings in Diabetic Retinopathy", Arch Ophthalmol–vol. 100, Mar. 1982, pp. 432–434.

Masataka Takahashi, MD et al., "Biomicroscopic Evaluation and Photography of Posterior Vitreous Detachment", Arch Ophthalmol–vol. 98, Apr. 1980, pp. 665–668.

James F. Vander, MD et al., "A Method For Induction of Posterior Vitreous Detachment During Vitrectomy", Retina 12:172–173, 1992.

Kang et al."Induction of Posterior Vitreous Detachment With Dispase In Rabbit Eyes", IOVS, Mar. 15, 1998, vol. 39, No. 4, 1769–B650, p. S379.

E.M. Frenzel et al., Effective Induction of PVR in Rabbits With Intravitreal Dispase, IOVS, Mar. 15, 1998, vol. 39, No. 4, 510–B433, S110.

Hiroshi Tagawa, MD et al., "Role of the Vitreous in Diabetic Retinopathy", Ophthalmology, Sep. 1986, vol. 93, No. 9, pp. 1188–1192.

Takahashi, MD et al., "Vitreoretinal Relationship in Diabetic Retinopathy", Arch Ophthalmol–vol. 99, Feb. 1981, pp. 241, 243, 244.

H. Quiroz et al., "Enzymatically Induced Posterior Vitreious Detachment", IOVS, 1984, vol. 25 (suppl.), p. 307.

G. S. Hageman et al., "Chondroitinase–Mediated Disinsertion of the Primiate Vitreous Body", IOVS, Mar. 15, 1994, vol. 35, No. 4, p. 1260.

Brian Matsumoto et al., "Topographic Variations in the Rabbit and Primate Internal Limiting Membrane", Investigative Ophthalmology & Visual Science, Jan. 1984, pp. 71–82.

Avni Murat Avunduk et al., "The Effect of Posterior Vitreous Detachment on the Prognosis of Branch Retinal Vein Occulusion", ACTA Ophthalmologica Scandinavica 1997, pp. 441–442.

R. Bruce Credo, PhD et al., "Fibrinolytic Mechanism, Biochemistry, and Preclinical Pharmacology of Recombinant Prourokinase", Journal of Vascular and Interventional Radiology, Nov.–Dec. 1995, vol. 6, No. 6, Part 2, pp. 8S–18S.

Arthur A. Sasahara, MD et al., "Clinical Studies With the New Glycosylated Recombinant Prourokinase", Journal of Vascular and Interventional Radiology, Nov.–Dec. 1995, vol. 6, No. 6, Part 2, pp. 84S–93S.

Robert W. Snyder, MD et al., "Intraocular Fibrinolysis With Recombinant Human Tissue Plasminogen Activator", Arch Ophthalmol–vol. 105, Sep. 1987, pp. 1277–1280.

Jun Akiba et al., "Molecular Mechanisms of Posterior Vitreous Detachment", Graefe's Arch Clin Exp Ophthalmol, 1993, 231: 408–412.

Thierry C. Verstraeten, MD et al., "Pharmacologic Induction of Posterior Vitreous Detachment in the Rabbit", Arch Ophthalmol, vol. 111, Jun. 1993, pp. 849–854.

George A. Williams, MD et al., "Treatment of Postvitrectomy Fibrin Formation With Intraocular Tissue Plasminogen Activator", Arch Ophthalmol, vol. 106, Aug. 1988, pp. 1055–1058.

S.A. Alba et al., "Intravitreal Hyaluronidase and Posterior Vitreal Detachment In The Rabbit", IOVS, 1998, vol. 39, No. 4, p. S829.

Robert Y. Foos, MD et al., "Vitreoretinal Juncture, Synchysis Senilis and Posterior Vitreous Detachment", Americans Academy of Ophthalmology, pp. 1502–1511, (1982).

Tongalp H. Tezel, MD et al., "Posterior Vitreous Detachment With Dispase", Retina, The Journal of Retinal and Vitreous Diseases, 1998, vol. 18, No. 1, pp. 7–15.

Mark Harooni, MD et al., "Efficacy and Safety of Enzymatic Posterior Vitreous Detachment By Intravitreal Injection of Hyaluronidase", Retina, The Journal of Retinal and Vitreous Diseases, 1998, vol. 18, No. 1, pp. 16–21.

(List continued on next page.)

Primary Examiner—Francisco Prats
(74) Attorney, Agent, or Firm—Roylance, Abrams, Berdo & Goodman, L.L.P.

(57) ABSTRACT

A process for inducing posterior vitreous detachment and for dissolving blood clots in the vitreous introduces a composition into the ocular cavity of an eye of a subject. The composition includes plasminogen and a plasminogen activator enzyme in amounts sufficient to induce substantially complete posterior vitreous detachment from the retina without causing inflammation of the retina and to dissolve blood clots in the vitreous. Suitable plasminogen activator enzymes include urokinase, streptokinase and tissue plasminogen activator.

3 Claims, 1 Drawing Sheet

OTHER PUBLICATIONS

Robert Y. Foos, MD et al., "Surface Structure of the Optic Nerve Head, Vitreopapillary Attachments and Posterior Vitreous Detachment", American Journal of Ophthalmology, Nov. 1973, vol. 76, No. 5, pp. 662–671.

Toshihiko Kohno et al., "Immunofluorescent Studies of Fibronectin and Laminin in the Human Eye", Investigative Ophthalmology & Visual Science, Mar. 1987, vol. 28, No. 3, pp. 506–514.

Clement K. Chan, MD et al., "Treatment of Idiopathic Macular Holes By Induced Posterior Vitreous Detachment", Ophthalmology, vol. 102, No. 5, May 1995, pp. 757–767.

Suzanne Lee, MD et al., "Effect of Urokinase on Posterior Penetrating Eye Injuries", Can J Ophthalmol, vol. 20, No. 7, 1985, pp. 251–253.

Elisabeth J. Cohen, MD, "Spontaneous Resolution of a Full–Thickness Macular Hole With Good Visual Acuity," Arch Ophthalmol, vol. 115, Jan. 1997, p. 130.

Jeff Koziol, M.D. et al., "Urokinase in Experimental Vitreous Hemorrhage", Ophthalmic Surgery, Fall 1975, vol. 6, No. 3, pp. 79–82.

Louise Cope Moorhead, MD, et al., "Bacterial Collagenase", Arch Ophthalmol, vol. 98, Oct. 1980, pp. 1829–1839.

J. Gartner, "Electron–microscopic study on the fibrillar network and fibrocyte–collagen interactions in the vitreous cortex at the ora serrata of human eyes with special regard to the role of disintegrating cells", 1986 Academic Press Inc. (London) Limited, pp. 21–33.

Yanina T. Wachtfogel et al., "Fibronectin Degradation Products Containing the Cytoadhesive Tetrapeptide Stimulate Human Neutrophil Degranulation", The American Society for Clinical Investigation, Inc., vol. 81, May 1988, pp. 1310–1315.

Laurence W. Gordon, MD et al., "Full–thickness Macular Hole Formation in Eyes with a Pre–existing Complete Posterior Vitreous Detachment", The Retina Institute of Maryland, Baltimore, pp. 1702–1705, (1995).

Taiichi Hikichi, MD et al., "Effect of the Vitreous on the Prognosis of Full–thickness Idiopathic Macular Hole", American Journal of Ophthalmology 116; pp. 273–278, (1993).

Toshihko Kohno, "Alterations in the Distribution of Fibronectin and Laminin in the Diabetic Human Eye", Investigative Ophthalmology & Visual Science, Mar. 1987, vol. 28, pp. 515–520.

Alan M. Roth, M.D. et al., "A System for the Macroexamination of Eyes in the Laboratory", A.J.C.P., vol. 59, May 1973, pp. 674–683.

L.A. Liotta et al., "Effect of Plasminogen Activator (Urokinase), Plasmin, and Thrombin on Glycoprotein and Collagenous Components of Basement Membrane", Cancer Research, vol. 41, pp. 4629–4634, (1981).

J. Akiba et al., Grateful Med Search Results, pp. 1–4. Akiba J. et al. Molecular Mechanisms of Posterior Vitreous Detachment. Graefes Arch Clin Exp Opthalmol Jul. 1993; 231(7): 408–12.

* cited by examiner

PROCESS AND COMPOSITION FOR INDUCING POSTERIOR VITREOUS DETACHMENT

FIELD OF THE INVENTION

The present invention is directed to a process and composition for producing posterior vitreous detachment in the eye of an animal. More, particularly invention relates to a process of introducing a mixture of plasminogen and a plasminogen activator to induce posterior vitreous detachment in the eye and to dissolve blood clots in the vitreous.

BACKGROUND OF THE INVENTION

Vitreous traction is the attachment of vitreous fibrils to the basement membrane of the retina by cellular and molecular interactions between components of the vitreous and the inner limiting membrane. Fibronectin and laminin are extracellular glycoproteins which are known to be the most important components of the attaching mechanism for stabilizing the vitreoretinal attachment. The vitreous is a clear, proteinaceous material which fills the posterior of the eye between the lens and the retina. The vitreous is attached at its posterior face to the retina at the vitreoretinal junction along the inner limiting membrane. The vitreoretinal junction is a layer of basement membrane proximal to the vitreous.

The inner limiting membrane of the retina contains type I and type II collagen, laminin, fibronectin and glycoconjugates. These components have been found to bind collagen fibers between the vitreous and the inner limiting membrane.

Vitreous traction is recognized as a serious and potentially blinding complication in a number of vitreoretinal diseases following vitreoretinal surgery. An important aspect of most vitreoretinal surgery is to relieve the vitreous traction. Improvements have been made in mechanical vitrectomy techniques and instrumentation. However, the complete removal of the cortical vitreous from the retinal surface continues to be a difficult task. In some vitreoretinal proliferative disorders, surgical removal of the cortical vitreous can result in retinal break formation or bleeding from traction on retinal blood vessels.

Numerous studies have been conducted to develop a chemical system to separate the vitreoretinal interface without damage to the retina. These studies typically evaluate the vitreoretinal interface and have devised various pharmacological methods for inducing a traumatic separation between the vitreous and the retina. Intraoperative complications, such as retinal tears and hemorrhage can occur during surgical hyaloidectomy.

A number of enzymes and chemical substances have been used to induce posterior vitreous detachment. For example, chondroitinase did not show any activity but both hyaluronidase and Alpha-chymotrypsin caused posterior vitreous detachment. However, these enzymes produced peripapillary and vitreous hemorrhage in these eyes. Dispase, hyaluronidase, Alpha-chymotrypsin, collagenase, chondroitinase, and expansile gas are pharmacological agents used to induce PVD. Dispase has been used in human and porcine cadaver eyes to separate the attachment of the posterior hyaloid from the inner limiting membrane. Dispase induced posterior vitreous detachment with minor morphologic changes in the inner retina. However, dispase, at low concentrations of 0.05–0.07 U, can cause proliferative vitreoretinopathy in 94% of cases up to 21 days after intravitreal injection. Doses equal to or higher than 0.05 U dispase can cause histologic epiretinal cellular membranes in all animals and 25% to 50% cataract formation which is related to dispase concentration. Some toxicity to the inner layer of the retina 15 minutes after injection of dispase has been reported, in spite of inducing posterior vitreous detachment. Intravitreal injection of hyaluronidase induced PVD in rabbits. The probable mechanism of inducing posterior vitreous detachment using hyaluronidase is vitreous liquefaction.

One study of a pharmacological method of inducing posterior vitreous detachment is described by Verstraeten et al *Arch. Ophthalmol.*, vol. 111, June 1993. This study evaluated the effectiveness of plasmin, which is a serine protease, in cleaning the vitreoretinal interface between the posterior vitreous cortex and the internal limiting membrane. The results showed some vitreous detachment and the presence of inflammatory cells. Other studies reported the application of plasmin in the vitreous in pediatric macular hole cases. A less traumatic separation of the vitreous from the retina and optic nerve head was induced by the injection of plasmin intravitreally immediately prior to vitrectomy. Plasmin and a plasminogen activator were evaluated for their effect on the basement membrane where plasmin was shown to be effective in degrading laminin and fibronectin which are found at the vitreoretinal junction and play an important role in vitreoretinal attachment. These processes did not however, produce complete posterior vitreous detachment.

Another example of efforts to induce posterior vitreous detachment is disclosed in U.S. Pat. No. 5,722,428 to Kaplan et al. In this process dispase is selected to specifically clean type IV collagen and fibronectin. The dispase is injected into the eye to promote posterior vitreous detachment. This process was shown to be ineffective in including complete vitreous detachment.

Accordingly, there is a continuing need for an effective process for inducing total or complete posterior vitreous detachment.

SUMMARY OF THE INVENTION

The present invention is directed to a composition and process for inducing posterior vitreous detachment in the eye. More particularly, the invention is directed to a process of introducing a combination of plasminogen and a plasminogen activator into the eye to induce posterior vitreous detachment.

Accordingly, a primary object of the invention is to provide a composition and process for inducing posterior vitreous detachment that is efficient and effective.

Another object of the invention is to provide a composition and process for inducing substantially complete posterior vitreous detachment of the vitreous from the inner limiting membrane of the retina.

A further object of the invention is to provide a process of inducing posterior vitreous detachment substantially without intraocular inflammation, electroretinography abnormalities or histologic abnormalities.

Another object of the invention is to provide a composition for separating the vitreous from the retina.

A further object of the invention is to provide a composition and process for dissolving blood clots in the vitreous.

The objects of the invention are basically attained by providing a process for inducing posterior vitreous detachment of the vitreous from the inner limiting membrane of an eye, comprising the step of introducing a composition of plasminogen and a plasminogen activator into the vitreous of an eye of an animal, said plasminogen and plasminogen activator being introduced in an effective amount to induce posterior vitreous detachment and said plasminogen activator being present in an amount to stimulate the conversion of plasminogen to plasmin.

The objects of the invention are further attained by providing a composition for inducing posterior vitreous detachment in the eye of an animal comprising plasminogen and a plasminogen activator enzyme in an amount sufficient to convert said plasminogen to plasmin, said plasminogen and plasminogen activator being present in amounts to induce substantially complete posterior vitreous detachment from the retina without causing inflammation.

The objects of the invention are also attained by providing a process for dissolving blood clots in the vitreous, comprising injecting a composition into the vitreous of the eye in an effective amount to dissolve blood clots present in the vitreous, the composition comprising a mixture of plasminogen, a plasminogen activator enzyme and an ophthalmologically acceptable carrier.

Other objects, advantages and salient features of the present invention will become apparent from the following detailed description, which, taken in conjunction with the annexed drawings, discloses a preferred embodiment of the invention.

BRIEF DESCRIPTION OF THE DRAWING

Referring to the drawing which forms a part of this original disclosure in which.

DETAILED DESCRIPTION OF THE INVENTION

Figure 1:
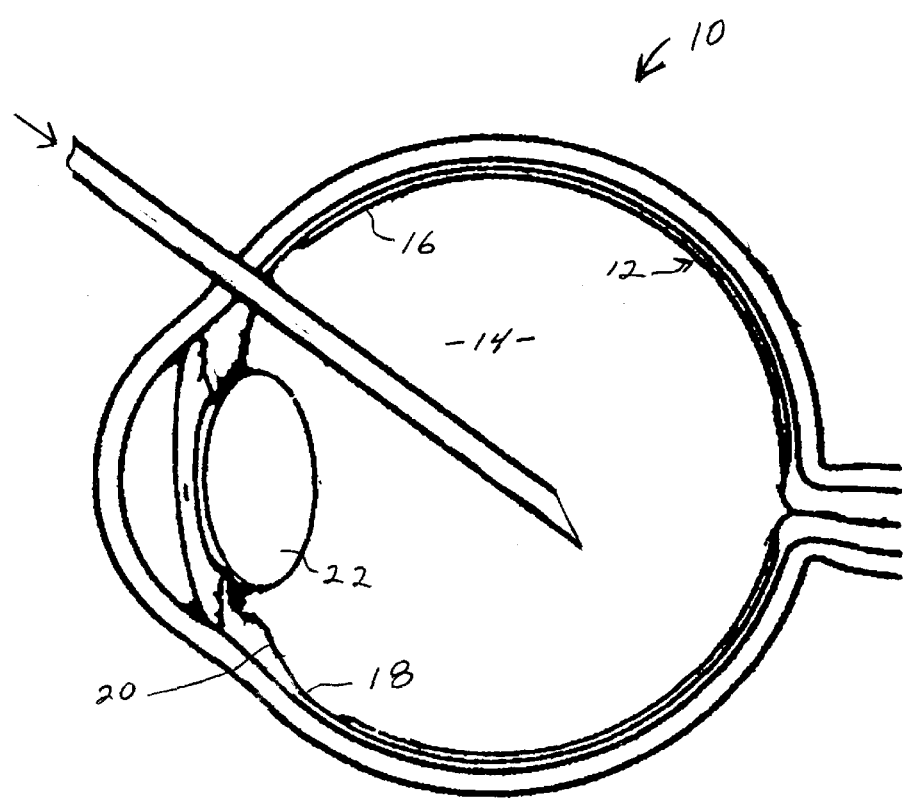
FIG. 1 is diagram in cross section of an eye shown a delivery device for introducing the composition to the eye.

The present invention relates generally to a composition and process for inducing posterior vitreous detachment. More particularly, the invention is directed to a composition and process for inducing posterior vitreous detachment without causing toxic effects on the retina. The invention is further directed to a composition and process for dissolving blood clots in the vitreous of an eye.

The process of the invention introduces a composition into the vitreous of the eye to induce complete posterior vitreous detachment and to dissolve blood clots. The composition includes plasminogen and a plasminogen activator for converting the plasminogen to plasmin or stimulating the release of plasmin in the eye. The preferred activator is urokinase although other enzymes such as streptokinase can be used. Although the mechanism for inducing posterior vitreous detachment is not completely understood, the plasminogen and activator have been found to produce cleavage at the vitreoretinal interface between the posterior vitreous cortex and the inner limiting membrane.

The composition preferably contains a nontoxic amount of plasminogen in a pharmaceutically acceptable carrier. It has been discovered that plasminogen in combination with urokinase or other plasminogen activators can be introduced into the vitreous at a dose such that substantially complete posterior vitreous detachment occurs without inflammation, and without ERG or histologic abnormalities. The dosages herein are expressed in terms of international units (IU). The plasminogen dispersed in an ophthalmologically suitable carrier is generally introduced into the vitreous of the eye at a dose of about 0.01 units to about 16.0 units. The plasminogen is generally introduced at a dose of about 2.0 units or less and at a dose of at least about 0.1 units. It has been found that prolonged exposure at dosages of plasminogen greater than 2.0 units can cause inflammation of the retina, while a dosage of less than 0.1 units of plasminogen is only partially effective in inducing complete posterior vitreous detachment within a 12 hour period.

The amount of the plasminogen introduced into the vitreous can vary depending on various factors. Low levels of plasminogen can be used to induce a slow rate of posterior vitreous detachment where the plasminogen remains in the eye for long periods of time. Alternatively, high doses of plasminogen can be used to induce a rapid posterior vitreous detachment. For example, plasminogen at doses of 4 units and 6 units can be introduced into the vitreous which induce posterior vitreous detachment in several hours. At higher doses of plasminogen greater than about 2 units, the plasminogen can cause inflammation of the retina. Therefore, at higher dosages, it is generally preferred to introduce the plasminogen composition for sufficient time to induce the desired extent of posterior vitreous detachment and then remove the vitreous and/or the plasminogen composition from the eye to prevent or minimize inflammation of the retina or other abnormalities. Standard vitrectomy surgical techniques are typically used to remove the vitreous from the eye and replace the vitreous with an ophthalmologically acceptable solution to stabilize the ocular cavity.

The plasminogen activator is an enzyme capable of stimulating the conversion of plasminogen to plasmin in the eye. The activator is preferably an enzyme that is capable of dissolving blood clots. The preferred enzyme is urokinase, although other enzymes, such as streptokinase and human tissue plasminogen activator (TPA), can be used.

Urokinase is preferably included to provide a dose of at least about 500 IU and less than about 2500 IU. In preferred embodiments, the composition contains about 1,000 IU since this dosage has been found effective in converting the plasminogen to plasmin in the eye and is effective in inducing posterior vitreous detachment without causing inflammation. It has been found that a dose of 5,000 IU or more can cause inflammation of the retina. The higher doses of the enzyme activator can activate the plasminogen normally present in the tissue. Tissue plasminogen activator (TPA) is used at a dose of about 25 micrograms or less. It has been found that tissue plasminogen activator used at dosages greater than 25 micrograms can be toxic in the eye. Streptokinase is typically used at dosages similar to the dosages for urokinase.

Previous studies of the vitreoretinal junction and the inner limiting membrane of the retina demonstrated that vitreous fibrils are attached to the basement membrane of the retina by cellular and molecular interactions between the various components of the vitreous and the inner limiting membrane. The attachment of the vitreous to the inner limiting membrane is primarily by fibronectin and laminin.

The inner limiting membrane contains type I and IV collagen, laminin, fibronectin and glycoconjugates that bind collagen fibers between the vitreous and the inner limiting membrane. Immunofluorescent studies have demonstrated the presence of fibronectin in the vitreous cortex and the inner limiting member. However, laminin is found only in the basement membrane components of the inner limiting membrane and associated with collagen type IV. Immunofluorescence studies further show that the laminin and fibronectin are found along the periphery of the retina and the ora serrata. These bands are generally thicker in the posterior retina, especially in younger people. The size of the bands shows a direct correlation to the age of the person.

The effect of plasmin on glycoprotein and the collagenous component of basement membrane has been studied. Plasmin may play a role in removing the glycoprotein components of the basement membrane including the fibronectin and laminin. Plasmin can expose the type IV collagen to degradation by different enzymes such as collagenase and elastase, but cannot by itself degrade the collagenous component of the basement membrane. Proteolysis of the laminin and the fibronectin found in the vitreous and on the retinal surface may play a very important role in inducing posterior vitreous detachment. However, plasmin by itself is not able to induce posterior vitreous detachment.

Urokinase is a serine protease which has been suggested to play a role independent of plasminogen effects. Previous efforts have shown that urokinase failed to produce significant degradation of fibronectin or other basement membrane components. In vitro studies revealed that urokinase may have some effects on the cell membrane associated fibronectin-binding site.

Some studies of posterior vitreous detachment found no correlation between fibronectin and laminin distribution and the occurrence of posterior vitreous detachment. Posterior vitreous detachment is not simply a thickening of the inner limiting membrane, but rather a complex phenomenon. Plasmin may facilitate the formation of posterior vitreous detachment by the proteolysis of laminin and fibronectin. Plasmin has some additional secondary effects against attachment of the vitreoretinal interface. Plasmin has an indirect activating effect on collagenase and may trigger release of elastase, which digests type IV collagen. Elastase is released from the PMNL which induces an inflammatory process. The use of plasmin alone in prior studies was shown to produce reversible ERG depression by the third day after injection due to hyperosmolarity of plasmin solution and also cause inflammation in the eye without retinal damage.

The process of the invention utilizes the combination of plasminogen and an enzyme for activating plasminogen. The preferred plasminogen activator is urokinase although other enzymes can be used. For example, streptokinase and tissue plasminogen activator can be used to convert the plasminogen to plasmin. The enzyme is found to have a synergistic effect when combined with plasminogen and introduced into the eye since plasmin alone and urokinase alone are not able to induce total posterior vitreous detachment, and can cause inflammation of the retina at high doses. The present invention is directed to the discovery that plasminogen when used in combination with an enzyme activator, such as urokinase, produces total and complete posterior detachment at nontoxic levels.

Plasmin is unstable and must be utilized rapidly to minimize converting to an inactive form. In embodiments of the invention, the plasminogen is combined with a plasminogen activator enzyme in a suitable ophthalmic carrier prior to injecting into the vitreous of the eye. The composition containing both the plasminogen and the plasminogen activator will produce plasmin in situ or just prior to injecting so that it is desirable to introduce the composition into the vitreous of the eye immediately after mixing to minimize conversion of the plasmin to the inactive form. Plasmin is produced in situ in the eye by the reaction between the plasminogen and the activator composition, as well as the reaction between the tissue plasminogen and the activator. In further embodiments of the invention, the plasminogen and the plasminogen activator are delivered to the vitreous of the eye simultaneously or sequentially through separate delivery devices. Alternatively, the plasminogen and plasminogen activator can be supplied to a common delivery device so that they mix as they are being introduced into the eye. Typically, the delivery device is a syringe suitable for injecting materials into the eye.

FIG. 1 illustrates an embodiment of the invention showing an eye 10, retina 12 and vitreous humor 14. The strongest adhesion between the vitreous 14 and the retina 12 occurs at the vitreous base 16. The vitreous base 16 is associated with the or a serrata 18 and the pars plana 20. The vitreous 14 is also attached at the peripheral central retina and at the posterior of the lens 22. The attachment at these locations is generally less than at the ora serrata 18 and the pars plana 20. Strong adhesion areas are also found around the optic nerve head and macula. As shown in FIG. 1, a delivery device, such as a needle, is inserted into the vitreous and the composition is introduced through a delivery device.

Generally, the composition is injected to the center of the vitreous although the composition can be introduced to other areas as known by those skilled in the art. The composition can be administered intravitreal, subvitreal, sublenticular, and in the posterior chamber of the eye.

In embodiments of the invention, the plasminogen and plasminogen activator are introduced into the vitreous humor of the eye prior to or in combination with intraocular surgery to induce posterior vitreous detachment prior to surgery. Examples of surgical procedures where posterior vitreous detachment is induced include vitrectomy for macular hole surgery, vitrectomy for diabetic reinopathy and other proliferative vascular retinopathies, repair and prevention of retinal detachment, subretinal surgery submacular surgery and retinal transplantation. The inducement of posterior vitreous detachment can also be used to treat blinding complications such as diabetic retinopathy, central vein occlusion, proliferative vitreoretinopathy and proliferative vascular retinopathy.

The plasminogen and the plasminogen activator composition are suspended or dispersed in a suitable carrier for introducing into the eye of a subject. Suitable carriers are nontoxic to the eye or the subject and do not inhibit the detachment of the vitreous from the retina. The carrier can include various salts, buffering agents, preservatives, compatible carriers and other therapeutic components such as steroids, antibiotics and anti-inflammatory agents as known in the art. Preferably, the carrier is a sterile liquid having a pH and osmolarity that are compatible with the normal vitreous. Suitable carriers include balanced salt solution, phosphate buffered saline lactated Ringer's solution and the like as known in the art. The resulting suspension generally contains, for example, about 0.1 units to about 25 units per ml of plasminogen.

Various antibiotics can be used in conjunction with the plasminogen and plasminogen activator. Suitable antibiotics include amikacin, dexamethasone, vancomycin, and mimocycline and derivatives thereof such as minocin, klimomycin, minomycin and vetrin. Amikacin is typically injected into the vitreous at a dose of about 200 micrograms. Dexamethasone, klinomycin and vancomycin are typically used in amounts of about 500 micrograms.

The composition of the invention can also be used in combination with other enzymes or agents which do not induce complete posterior vitreous detachment when used alone. For example, the composition can be used in conjunction with enzymes, such as at least one selected from the group consisting of a chondroitinase (chondroitinase ABC or AC), dispase and, α-thrombin and transglutaminase. It is believed that these compounds have a synergistic effect when used simultaneously with the combination of plasminogen and a plasminogen activator enzyme.

The plasminogen and plasminogen activator are introduced into the eye in amounts to induce complete or substantially complete posterior vitreous detachment without causing inflammation of the retina or other adverse side effects. The suspension or dispersion is typically injected into the eye in an amount of about 0.1–0.5 ml. The amounts of the respective components can vary depending on the condition being treated, the pH and condition of the vitreous and the time requirements for attaining vitreous detachment. The volume of the eye and the age of the subject are also factors in determining the amount of components introduced. In further embodiments of the invention, the plasminogen and plasminogen activator composition can be introduced into the eye an amount sufficient to attain a desired degree of vitreous detachment which may be less than complete detachment.

EXAMPLE I

Test samples were prepared to compare the effects of plasminogen alone, urokinase alone and a combination of plasminogen and urokinase on the eye. A stock solution of low molecular weight, purified recombinant urokinase was obtained from Abbott Laboratories, North Chicago, Ill. having a concentration of 407,000 IU/ml. This solution was diluted with balanced salt solution to produce solutions having 10,000 IU/ml, 5,000 IU/ml, and 1,000 IU/ml.

Purified human plasminogen was obtained having a concentration of 220 caseinolytic units (CU) per milliliter. The plasminogen was diluted in balanced salt solution to form solutions having the concentrations set forth in Table 1. Additional samples solutions were prepared containing 1,000 units urokinase and concentrations of plasminogen ranging from 0.1 to 2.0 units as set forth in Table 1.

Albino New Zealand rabbits weighing approximately 2 Kg were used in this example and were treated according to ARVO resolution for use of animals in research. A detailed ophthalmological examination was performed on the rabbits with indirect ophthalmoscope and slit lamp biomicroscopy using a 60-diopter lens. Only normal rabbits were used in this experiment.

The rabbits were divided into three groups and anesthetized using 50 mg/kg Ketamine and 5 mg/kg xylazine. The conjunctiva were sterilized with 5% povidone iodine and rinsed with a balanced salt solution. Anterior chamber paracentesis was performed just prior to injection to prevent hypertension.

The right eye of each rabbit was injected with samples of Table 1 using a tuberculin syringe fitted with a 30-gauge needle. The samples were injected 3 mm posterior to the limbus into the midvitreous cavity under direct observation. The Group I rabbits were injected intravitreally with pure urokinase at a dose of 1,000 IU, 5,000 IU and 10,000 IU. The Group II rabbits were injected intravitreally with recombinant plasminogen at a dose of 0.1, 0.4, 1.0, 2.0, 4.0, 8.0, 16.0 caseinolytic units (CU). The Group III rabbits were injected intravitreally with a combination of 1,000 IU urokinase and nontoxic concentrations of 0.1, 0.4, 1.0, 2.0 units of plasminogen. The left eyes were injected with a balanced salt solution as control samples.

Electrophysiology

Electroretinography (ERG) recordings were performed before injection and then repeated 3 days and 15 days after injection. The rabbits were anesthetized and kept for 30 minutes in a dark room before ERG recordings. The UTAS-E 2000 system (LKC Technologies, Gaithersburg, Md.) was used for the ERG. The conjunctive and cornea were anesthetized with proparacaine 0.5%. Unipolar contact lenses were placed on both corneas with methylcellulose. The negative electrode was placed into the subcutaneous space of the forehead and the ground electrode was clipped to the earlobe with electric gel. Both dark adapted and light adapted stimulus were recorded. The average of three sweeps was taken for each step. B-wave amplitude after injection was compared to the preinjection value of the same eye. A decrease in b-wave amplitude of greater than 30% was considered significant.

Follow Up

The eyes were evaluated by slit lamp examination and indirect fundus ophthalmoscopy immediately after injection to detect any ocular trauma caused by the injection.

Detailed ophthalmologic examinations were done 30 minutes, 1, 2, 8, 12, and 24 hours and 3, 10, and 15 days after injection. Fundus photographs were taken at different times. B-mode ultrasonography (Innovative Imaging Inc. System, Sacramento, Calif.) was performed to reveal PVD.

Histology

The rabbits were sacrificed with an intravenous injection of sodium pentobarbital (100 mg/kg) 2 weeks after injection with the test samples. The eyes were enucleated and penetrated 2.5 mm posterior to the limbus to allow the fixative solution to fill the eyes rapidly. Eyes were fixed in 2% paraformaldehyde and 3% glutaraldehyde. After 24 hours of fixation, a hemidissection of the globe was performed at roughly the horizontal meridian using a thin, sharp blade. The incision was completed, dividing the globe into superior and inferior pieces which were inspected to ensure that the vitreous had been cut completely. Each piece of the globe was tilted, anterior segment down, and the vitreoretinal attachment was evaluated as described by Foos. If a total posterior vitreous detachment had occurred, the vitreous fell away from the retinal surface by gravity. If there was no posterior vitreous detachment or only partial separation, the vitreous was suspended from the eye cup.

Paraffin sections were stained with hematoxylin and eosin for evaluation of retinal toxicity and vitreoretinal interface features under a light microscope. Small pieces of retina, close to the optic nerve, were taken from both experimental and control eyes. The specimens were processed for transmission electron microscopy (TEM). Thin sections were stained with uranyl acetate and lead citrate and observed under a transmission electron microscope (EMTO C/Cr; Zeiss, Oberkochen, Germany). Special attention was paid to the inner limiting membrane (ILM) and collagen fiber attachment to the ILM.

The effects of the various samples on the eye are set forth in Table 1. The eyes injected with Samples 1 and 2 (10,000 IU and 5,000 IU urokinase) showed whitish-gray retinal lesions inferior to the optic disc in the posterior pole. Some minor retinal hemorrhage and dense vitreous inflammation were noticed in the eyes of Samples 1 and 2. Sample 3 containing 1,000 IU urokinase showed no vitreous haze, hemorrhage, inflammation, cataract or other complications.

The Group II Samples 4 and 5 containing 16 U and 8 U of plasminogen caused moderate to severe intraocular inflammation. Sample 6 containing 4.0 U of plasminogen resulted in a very limited amount of inflammation of the vitreous. Samples 7–10 containing 2.0 U, 1.0 u, 0.4 U and 0.1 U, respectively, showed no vitreous haze, hemorrhage inflammation or cataract.

The Group III Samples 11–14 containing 1,000 IU urokinase and 2.0 CU, 1.0 CU, 0.4 CU and 0.1 CU, respectively, showed no vitreous haze, hemorrhage, inflammation or cataract. In Samples 11–14, posterior vitreous detachment was detected ophthalmoscopically for the first time about 8 hours after injection. At 12 hours, all eyes of Samples 11 and 12 containing 2.0 CU and 1.0 CU plasminogen and 1.000 IU urokinase showed complete posterior vitreous detachment which was confirmed with ultrasonography. Sample 13 containing 0.4 CU plasminogen and 1.000 IU urokinase resulted in three eyes with total posterior vitreous detachment and one with partial posterior vitreous detachment. Sample 14 containing 0.1 CU plasminogen and 1.000 IU urokinase resulted in an eye with total posterior vitreous detachment and three eyes partial posterior detachment. All of the control eyes showed no posterior vitreous detachment.

Gross examination of enucleated eyes showed similar results to the results of the fundus examination. The vitreous fell away from the retina in all of the eyes of Samples 11 and 12. Three eyes of Sample 13 and one eye of Sample 14 showed total vitreous separation while the others showed partial separation.

Electrophysiology

ERG recordings demonstrated that doses of 5,000 to 10,000 IU of Samples 1 and 2 were toxic to the retina. The b-wave amplitudes in more than 60% in both doses when compared the preinjection value. The ERG results were normal for all eyes of Samples 4–10 of Group II and Samples 11–14 of Group III although the eyes of Samples 4–6 showed inflammation.

Light Microscopy

Histologic sections of eyes of Samples 1 and 2 containing 10,000 IU and 5,000 IU urokinase showed intensive disorganization of the retina. The eyes of sample 3 containing 1,000 IU urokinase showed normal retinal structure.

In Group II Samples 4–6, respectively showed minimal, moderate and severe intraocular inflammatory cell response in the vitreous. Samples 7–10 were normal. However, no posterior vitreous detachment was observed. Control eyes were normal and showed no posterior vitreous detachment.

The Samples 11–14 of Group III showed separation of the vitreoretinal interface depending on the plasminogen concentration. Complete posterior vitreous detachment was observed in all eyes of Samples 11 and 12. Sample 13 showed complete posterior vitreous detachment in three eyes with partial detachment in the other. Sample 14 showed complete detachment in one eye and partial detachment in the remaining three.

Electron Microscopy

Group 3 eyes of Samples 11–14 showed empty vitreous cavities and smooth internal surfaces of the retina. No collagen fibers were seen adjacent the retinal surface. The control showed persistent vitreous collagen fibers attached to the retinal surface.

TABLE 1

| Drug Dose | | | | | | |
|---|---|---|---|---|---|---|
| Urokinase | Plasminogen | Vol. | No. of Eyes | No. of Total PVD | No. of Partial PVD | Inflammation |
| Group I | | | | | | |
| Sample 1 | 10,000 IU | — | 0.1 ml | 4 | 0 | 0 | yes |
| Sample 2 | 5,000 IU | — | 0.1 ml | 4 | 0 | 0 | yes |
| Sample 3 | 1,000 IU | — | 0.1 ml | 4 | 0 | 0 | no |
| Group II | | | | | | |
| Sample 4 | — | 16.0U | 0.1 ml | 4 | 0 | 0 | yes |
| Sample 5 | — | 8.0U | 0.1 ml | 4 | 0 | 0 | yes |
| Sample 6 | — | 4.0U | 0.1 ml | 4 | 0 | 0 | yes |
| Sample 7 | — | 2.0U | 0.1 ml | 4 | 0 | 0 | no |
| Sample 8 | — | 1.0U | 0.1 ml | 4 | 0 | 0 | no |
| Sample 9 | — | 0.4U | 0.1 ml | 4 | 0 | 4 | no |
| Sample 10 | — | 0.1U | 0.1 ml | 4 | 0 | 4 | no |
| Group III | | | | | | |
| Sample 11 | 1,000 IU | 2.0U | 0.1 ml | 4 | 4 | 0 | no |
| Sample 12 | 1,000 IU | 1.0U | 0.1 ml | 4 | 4 | 0 | no |
| Sample 13 | 1,000 IU | 0.4U | 0.1 ml | 4 | 3 | 1 | no |
| Sample 14 | 1,000 IU | 0.1U | 0.1 ml | 4 | 1 | 3 | no |
| Control (Balanced Salt Solution) | — | — | 0.1 ml | 56 | 0 | 0 | no |

Although the invention has been described with a certain degree of particularity, it is understood that the present disclosure has been made only by way of example and that numerous changes in the details of construction and the combination and arrangement of parts may be resorted to without departing from the spirit and scope of the invention. Thus, the scope of the invention should not be limited by the foregoing specification, but rather, only by the scope of the claims appended hereto.

What is claimed is:

1. A process for inducing substantially complete posterior vitreous detachment of the vitreous from the retina in the eye of an animal, said process comprising the step of injecting a non-toxic composition into the vitreous of said eye in an effective amount to induce substantially complete posterior vitreous detachment in said eye without intraocular inflammation, said composition comprising about 0.01 units to about 16.0 units plasminogen, about 500 units to about 2500 units urokinase, transglutaminase and a pharmaceutically acceptable carrier.

2. The process of claim 1, wherein said process comprises injecting said urokinase at a dose of about 1,000 U.

3. The process of claim 1, further comprising the step of injecting said composition into the vitreous of the eye in an effective amount to dissolve blood clots, and dissolving blood clots in the vitreous.

* * * * *